(12) United States Patent
Foucault

(10) Patent No.: US 10,398,825 B2
(45) Date of Patent: Sep. 3, 2019

(54) FILTER MEDIUM FOR OBTAINING PLASMA, AND ASSOCIATED FILTRATION DEVICE AND METHOD

(71) Applicant: BIOMERIEUX, Marcy l'etoile (FR)

(72) Inventor: Frederic Foucault, Marcy l'etoile (FR)

(73) Assignee: BIOMERIEUX, Marcy l'Etoile (FR)

( * ) Notice: Subject to any disclaimer, the term of this patent is extended or adjusted under 35 U.S.C. 154(b) by 448 days.

(21) Appl. No.: 15/032,411

(22) PCT Filed: Nov. 13, 2014

(86) PCT No.: PCT/FR2014/052889
§ 371 (c)(1),
(2) Date: Apr. 27, 2016

(87) PCT Pub. No.: WO2015/071597
PCT Pub. Date: May 21, 2015

(65) Prior Publication Data
US 2016/0279551 A1 Sep. 29, 2016

(30) Foreign Application Priority Data
Nov. 14, 2013 (FR) ..................... 13 61140

(51) Int. Cl.
*A61M 1/34* (2006.01)
*B01D 39/20* (2006.01)

(52) U.S. Cl.
CPC ....... *A61M 1/3496* (2013.01); *B01D 39/2017* (2013.01); *B01D 2239/0407* (2013.01);
(Continued)

(58) Field of Classification Search
CPC ......... A61M 1/3496; B01D 2239/0407; B01D 2239/0414; B01D 2239/065;
(Continued)

(56) References Cited

U.S. PATENT DOCUMENTS

2012/0305500 A1* 12/2012 Bormann .......... B01L 3/502753
210/808

FOREIGN PATENT DOCUMENTS

EP 0392377 A2 10/1990
EP 0406485 A1 1/1991
(Continued)

OTHER PUBLICATIONS

Kersaudy-Kerhoas, M., et al., "Micro-scale blood plasma separation: from acoustophoresis to egg-beaters", The Royal Society of Chemistry 2013, 13, pp. 3323-3346.
(Continued)

*Primary Examiner* — John Kim
(74) *Attorney, Agent, or Firm* — Ladas & Parry LLP; Malcolm J. MacDonald

(57) ABSTRACT

The invention relates to a filter medium (31) comprising two porous zones arranged in the form of a stack:
a first porous zone (100), called "prefiltration", treated with at least one reagent presenting affinity for red blood cells and leading to red blood cells being captured or agglutinated on the prefiltration zone; and
a second porous zone (200), called "asymmetric", presenting pore size that decreases transversaly to its thickness, the portion of higher pore size being positioned towards the prefiltration zone (100). The invention also relates to systems, devices, and methods making use of the medium.

28 Claims, 5 Drawing Sheets

(52) U.S. Cl.
CPC ............... *B01D 2239/0414* (2013.01); *B01D 2239/065* (2013.01); *B01D 2239/1208* (2013.01); *B01D 2239/1216* (2013.01)

(58) Field of Classification Search
CPC .... B01D 2239/1208; B01D 2239/1216; B01D 39/2017
See application file for complete search history.

(56) References Cited

FOREIGN PATENT DOCUMENTS

| | | |
|---|---|---|
| EP | 0606646 A1 | 7/1994 |
| GB | 2 250 342 A | 6/1992 |
| WO | 2004018078 A1 | 3/2004 |

OTHER PUBLICATIONS

O'Farrell, B., "Introduction: History of Membrane-Based Point of Care Immunoassays", Lateral Flow Immunoassay 2009, pp. 1-33.
International Search Report dated May 27, 2015, corresponding to International Patent Application No. PCT/FR2014/052889.

\* cited by examiner

FILTER MEDIUM FOR OBTAINING PLASMA, AND ASSOCIATED FILTRATION DEVICE AND METHOD

This application is a 371 of PCT/FR2014/052889, filed on Nov. 13, 2014, which claims priority to French Patent Application No. 1361140, filed Nov. 14, 2013.

The present invention relates to the technical field of processing blood, in particular for extracting plasma from a blood sample, and specifically a sample of whole blood.

More precisely, the invention relates to a filter medium, to a filter system, and to a device containing such a filter medium and suitable for transferring a portion of a blood sample that is contained in a plugged container, and also to associated methods.

In the field of biological analysis of blood samples, it is common practice to recover a blood sample in a container that is in the form of a tube closed by a plug, such as a septum, that can be penetrated by a hollow needle. Numerous solutions have been proposed for obtaining plasma from such a sample of whole blood. Among other techniques, those solutions rely on two specific techniques for extracting plasma from blood, namely filtering and centrifuging.

Isolating blood plasma by centrifuging requires the use of equipment that is complex and expensive firstly for the purpose of separating the components of blood as a function of their density differences by subjecting them to centrifugal force, and secondly for extracting the plasma from the portion of the blood containing the red blood cells (erythrocytes) after they have had time to settle. Independently of the need to have recourse to a centrifuge and to centrifuge tubes, that technique requires centrifuging time that is relatively long, and it presents difficulty in defining the centrifugal force needed for obtaining plasma that does not contain any formed elements of blood.

Extracting plasma by filtering requires the use of a blood separation medium. The article "Micro-scale blood plasma separation: from acoustophoresis to egg-beaters", published in "The Royal Society of Chemistry 2013", summarizes the various known solutions for achieving plasma separation at microscopic scale. Among those techniques, mention may be made of those described in the following documents:

Document EP 0 392 377 describes a device for separating plasma or serum from a sample of whole blood that makes use of a filter including an agent for agglutinating blood cells; and Documents WO 2004/018078, EP 0 406 485, and EP 0 606 646 describe filters for eliminating white blood cells (leukocytes) from blood samples, corresponding to filters of asymmetric structure.

Human blood presents a hematocrit content that is variable depending on the activity and the health of the subject, in particular in the event of anemia or polycythemia. The greater the hematocrit content, the more difficult is the operation of filtering. In particular, problems are encountered concerning plugging/clogging, hemolysis, slow extraction rate.

An analysis of known prior techniques shows that there does not exist a simple solution leading to satisfactory filtering at low cost and with few operations, while limiting problems of plugging/clogging. In particular, the invention seeks to provide a filter medium that makes it possible to improve blood filtering significantly in order to obtain plasma, both in terms of quantity (greater volume in a given length of time) and in terms of quality (less hemolysis and better elimination of formed elements of blood).

In this context, the present invention provides a filter medium comprising two porous zones arranged in the form of a stack:

a first porous zone, called "prefiltration", treated with at least one reagent presenting affinity for red blood cells and leading to red blood cells being captured or agglutinated on the prefiltration zone; and a second porous zone, called "asymmetric", presenting pore size that decreases transversaly to its thickness, the portion of higher pore size being positioned towards the prefiltration zone.

The present invention also provides a filter system for filtering blood, in particular whole blood, enabling plasma to be recovered, the system comprising a chamber containing a filter medium of the invention and provided with an inlet for the blood to be filtered that is positioned towards the prefiltration zone, and with an outlet for plasma that is situated towards the asymmetric zone, the filter medium being positioned in the chamber in such a manner that the blood flows from the inlet to cross through both zones of the filter medium, with plasma being recovered at the outlet.

The invention also provides a method of obtaining plasma from a blood sample, and in particular a sample of whole blood, the method implementing a system of the invention in which the blood sample is introduced into the system via the inlet and plasma is recovered from the outlet.

There is also a need for a novel technique making it possible, without risk of contamination, to extract a non-negligible quantity of plasma relatively quickly from a closed container containing a blood sample, and in particular a sample of whole blood.

The invention thus seeks to satisfy this need by proposing a novel technique for extracting a portion of a blood sample contained in a plugged container in a manner that is simple and without risk of contamination, and in a time that is relatively short.

Thus, the invention also provides a device for transferring a portion of a blood sample, and in particular a sample of whole blood, contained in a container provided with a plug, and leading to plasma being recovered, the device being characterized in that it comprises:

a hollow needle provided with a proximal end with a distal end for penetrating through the plug of the container;

a pressure chamber for pressurizing a fluid and having the proximal end of the hollow transfer needle passing therethrough, the chamber being provided with a septum positioned to be penetrable by the proximal end of the needle after the needle has moved, the chamber being leaktight and separated by the septum from a liquid distribution chamber into which the proximal end of the hollow needle can open out; and an approach system for causing the hollow needle and the septum to approach each other so as to increase the pressure of the fluid as a result of said approach, the approach system being controlled to move over a determined stroke so that in a first stage the pressure inside the leaktight chamber is increased up to a transfer pressure immediately prior to the hollow needle passing through the septum, and in a second stage the hollow needle passes through the septum to open out into the blood distribution chamber that is at a pressure lower than the transfer pressure so that under the effect of this pressure difference a portion of the blood is transferred from the container into said distribution chamber, said distribution chamber including a filter system of the invention for extracting plasma.

The invention also seeks to propose a method making it possible from a single container to extract on several occasions non-negligible quantities of plasma from a blood sample, and in particular a sample of whole blood, contained in a container provided with a plug.

The invention also provides a method of transferring a portion of a blood sample, and in particular a sample of whole blood, contained in a container provided with a plug, the method enabling plasma to be recovered and being characterized in that it consists in:

using a hollow needle passing through the plug of the container to put the inside of the container into communication with a leaktight chamber for pressurizing a fluid, which chamber is provided with a septum that is penetrable by needle and presents a volume that is variable as a result of relative movement between the hollow needle and the septum that is penetrable by needle;

causing the hollow needle and the septum that is penetrable by needle to approach each other over a determined stroke so as to increase the pressure inside the chamber and consequently inside the container by transferring the fluid via the hollow needle and reaching a transfer pressure immediately prior to the hollow needle passing through the septum;

continuing to cause the hollow needle and the septum that is penetrable by needle to approach each other so that the hollow needle passes through the septum so as to open out into a blood distribution chamber at a pressure that is lower than the transfer pressure so that under the effect of this pressure difference a portion of the blood is transferred through the hollow needle from the container into said distribution chamber; and ensuring that the blood transferred into the distribution chamber flows through a filter system of the invention in order to extract plasma.

The following description given with reference to the accompanying figures enables the invention to be better understood.

Figure 1:
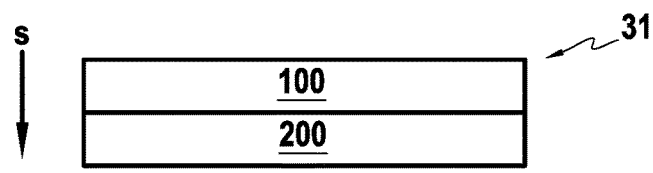
FIG. 1 is a diagrammatic section view of a filter medium of the invention.

According to an essential characteristic, the filter medium of the invention comprises two distinct zones: a zone referred to as a "prefiltration" zone for blocking red blood cells by a phenomenon of agglutination or of aggregate formation; and an "asymmetric" zone.

In order to perform its prefiltration function, and in conventional manner, the minimum size of the pores in the prefiltration zone is greater than the maximum size of the pores in the asymmetric zone. In the context of the invention, pore size can be measured using the ASTM standard F 316-80. The prefiltration zone presents a pore size greater than the size of the red blood cells, and preferably lying in the range 10 micrometers (μm) to 1 millimeter (mm); the asymmetric zone presents a pore size in its portion of maximum pore size that allows red blood cells to pass, for instance lying in the range 10 μm to 100 μm, and in its minimum pore size portion it has a pore size less than the size of blood cells, and in particular red blood cells, and preferably lying in the range 0.1 μm to 10 μm.

The material constituting the various zones is preferably selected so as to have a capacity for wetting that is adapted to blood penetrating and flowing. In particular, materials should be selected that present an appropriate critical wetting surface tension (CWST).

CWST can be measured using the Young-Dupré equation. A drop of liquid spreads out to a greater or lesser extent on the surface of a solid. This phenomenon is known as "wetting" and the term "contact angle" designates the angle between the fluid/gas interface and the solid surface. Measuring the angle of a drop of water is the reference method.

In advantageous manner, the prefiltration zone has critical wetting surface tension between $50 \times 10^{-3}$ newtons per meter (N·m$^{-1}$) and $100 \times 10^{-3}$ N·m$^{-1}$, and preferably greater than $53 \times 10^{-3}$ N·m$^{-1}$; naturally, these values relate to the prefiltration zone that carries reagents presenting an affinity for red blood cells. In a particular embodiment, the prefiltration zone is a fibrous medium. The fibers treated by having blood passed therethrough capture the red blood cells by affinity when they pass close to the fibers. This capture finishes off the physical filtering obtained by selecting the pore size for the prefiltration zone so as to retain a fraction of the blood cells as a function of their size. Advantageously, the prefiltration zone is made up of glass fibers presenting density lying in the range 50 grams per square meter (g·m$^{-2}$) to 300 g·m$^{-2}$.

Advantageously, the asymmetric zone has a critical wetting surface tension between $50 \times 10^{-3}$ N·m$^{-1}$ and $100 \times 10^{-3}$ N·m$^{-1}$, and preferably greater than $70 \times 10^{-3}$ N·m$^{-1}$. By way of example, the asymmetric zone is constituted by a porous material selected from synthetic polymers such as polysulfones, polycarbonates, polyesters, polyolefins, polyamines, polyacrylics, polyvinyls, and from inorganic materials such as glasses, ceramics, metals.

The prefiltration zone is present to retain the aggregates and the largest components present in the blood sample for filtering, and in particular in a sample of whole blood. This prefiltration zone acts as a first filter medium so as to reduce the initial red blood cell content of the blood sample. Given the number of red blood cells per milliliter (mL) and given the way they deform easily, in the context of the invention chemical prefiltration is selected since that makes it possible to limit or even completely avoid subsequent clogging of the asymmetric filter. This prefiltration also makes it possible to filter large volumes of blood, or indeed to perform several successive filtering operations on a single initial sample of whole blood.

This prefiltration zone uses a principle of filtration by affinity since specific bonding partners for red blood cells are present on the filter in order to capture them. The bonds that occur between the red blood cells and the reagents that present an affinity for red blood cells are low energy bonds of the Van der Walls, electrostatic, hydrogen, . . . type. The molecules or reagents that present an affinity for red blood cells lead to at least some of the red blood cells being captured or agglutinating on the prefiltration zone. Such molecules presenting an affinity for red blood cells may in particular be selected from antibodies specific to antigens present on red blood cells, and lectins, such as hemaglutinin. In particular, it is possible to use antibodies that are specific to an antigen that is to be found on the red blood cells of the blood group of the patient from whom the sample for analysis originates. Antibodies are said to be specific when they are capable of bonding in exclusive or almost exclusive manner with the target antigen.

Reagents presenting an affinity for red blood cells may be attached to the prefiltration zone by any appropriate technique. The filter that is to constitute the prefiltration zone may be treated chemically, in particular by grafting or by adsorption. Reference may be made in particular to Lateral Flow Immunoassay, edited by Raphael C. Wong, I. Harley, Y. Tse (ISBN: 978-1-58829-908-6), published in 2009, chapter 1.4.1.3, pages 12-13. Beforehand, it is possible to perform physical treatment of the type involving a plasma or irradiation, in particular under ultraviolet (UV) radiation in order to facilitate attaching reagents that present an affinity for red blood cells. Thus, the reagents that present an affinity for red blood cells may be adsorbed, bonded physically or chemically, on the surface and in the thickness of the prefiltration zone. Such filters are described in particular in Document GB 2 250 342. Usually, treatment is performed using a formulation including reagents presenting an affinity for red blood cells. Other molecules may be used in the formulation, such as wetting agents such as bovine serum albumin (BSA) and casein, also serving to prevent non-specific adsorption. By way of example, it is possible to use a deposition formulation containing a quantity of reagents presenting an affinity for red blood cells that corresponds to a concentration lying in the range 0.1 milligrams per milliliter (mg/mL) to 1 mg/mL.

The blood passes firstly through the prefiltration zone, and then the asymmetric zone. When the blood that has thus been depleted initially of red blood cells by passing through the prefiltration zone reaches the "asymmetric" zone, plasma extraction is made easier and more effective. Furthermore, the minimum pore size of the "asymmetric" zone is very small. The presence of a decreasing pore size gradient going from the prefiltration zone, i.e. in the blood flow direction, makes it possible to avoid accumulating red blood cells that remain at the inlet surface of the asymmetric zone and to avoid phenomena of hemolyses and clogging.

Usually, and as shown in FIG. 1 which is a diagram showing a filter medium 31, the prefiltration zone 100 and the asymmetric zone 200 are directly in contact with each other, although the possibility of inserting an intermediate zone should not be excluded. Within the asymmetric zone 200, the greatest pore size is in contact with the prefiltration zone 100. When the blood that flows in the direction s, that has thus already been depleted of red blood cells by passing through the prefiltration zone 100 reaches the asymmetric zone 200, that zone then enables plasma to be extracted more easily and more effectively.

In a particular embodiment, the filter medium is constituted exclusively by the prefiltration and asymmetric zones as defined in the context of the invention. Each of these zones may be constituted by only one filter element or by a plurality of filter elements. In particular, in order to obtain the desired thickness, the prefiltration zone may be constituted by a stack of a plurality of filter elements treated with the reagent(s) presenting an affinity for red blood cells, so as to obtain the desired thickness. It is also possible to envisage making a filter zone with at least one filter element that has been treated with the reagent presenting an affinity for red blood cells and one or more other filter elements of appropriate pore size.

Preferably, the various filter elements making up the prefiltration zone are identical. Specifically, it is preferred to have a prefiltration zone that is constituted by one or several elements but that presents pore size that is uniform across its thickness, as contrasted with the "asymmetric" zone.

Likewise, the asymmetric zone may be constituted by a single element presenting a pore size gradient across its thickness, such as the elements sold by the supplier Pall in its Vivid® range, or indeed a stack of different elements of different pore sizes that are selected in such a manner as to obtain the desired decrease. Under such circumstances, the decrease in pore size takes place stepwise.

The person skilled in the art can adjust the thickness of the various zones in order to optimize the pore size/thickness/area ratio and to minimize dead volume. In general, the prefiltration zone has thickness from 0.3 mm to 5 mm, and in particular from 1.2 mm to 3 mm, and/or the asymmetric zone presents thickness from 0.1 mm to 5 mm, and in particular from 0.2 mm to 3 mm.

The filter medium of the invention is particularly adapted to filtering whole blood. In conventional manner, the term "whole blood" designates a blood sample containing all of the constituents of blood (plasma, white and red blood cells, platelets, . . . ). A sample of whole blood may possibly include a coagulating agent. A filter medium may be used in particular on capillary blood (a drop of blood taken from the end of a finger). In particular, such a filter medium may be used in a test performed close to the patient, such as a rapid test.

In general, the filter medium is incorporated in a system for filtering blood, and in particular whole blood, that enables plasma to be recovered and that includes a chamber incorporating the filter medium and provided with an inlet for the blood for filtering that is positioned towards the prefiltration zone, and an outlet for plasma that is situated towards the asymmetric zone, the filter medium being positioned in the chamber in such a manner that the blood flows from the inlet to cross through both zones of the filter medium, with the plasma being recovered at the outlet. Such a filter system 30 could itself be incorporated in an extraction device that is more complex, such as shown in particular in FIGS. 2 to 7. It is also possible to envisage using the filter medium of the invention for sucking blood directly from a patient and then extracting the plasma. It is thus possible to perform blood analyses on plasma without making use of a tube for taking a sample of whole blood. Under such circumstances, suction needs to be applied to the filter medium itself, in particular in the form of a static or dynamic vacuum.

The device as shown in FIGS. 2 to 7, which constitutes one of the major applications of the filter medium of the invention, is described below in detail. As can be seen more clearly in FIGS. 2 and 3, such a device 1 is designed to transfer a portion of a blood sample 2 contained in a container 3 that is conventionally in the form of a tube that is hermetically closed by a plug 4. In general, the container 3 is a tube for taking a blood sample under a vacuum.

According to a characteristic of the device 1 of the invention, the container 3 is suitable for having a hollow needle 5 penetrating therein with a portion of the blood contained inside the container being transferred or extracted through the needle. The plug 4, such as a septum of a sample tube, can be penetrated by the hollow needle 5. As can be seen more clearly in FIGS. 3 and 6, the hollow needle 5 has a distal end 6 for penetrating through the plug 4 of the container and a proximal end 7 that performs a function that is described in greater detail in the description below. In the example shown in FIG. 6, the plug 4 of the container 3 has the distal end 6 of the hollow needle 5 passed therethrough as a result of relative movements of the container 3 and the hollow needle 5 towards each other. Naturally, provision could be made for the plug 4 to be fitted ab initio with the hollow needle 5.

Figure 2:
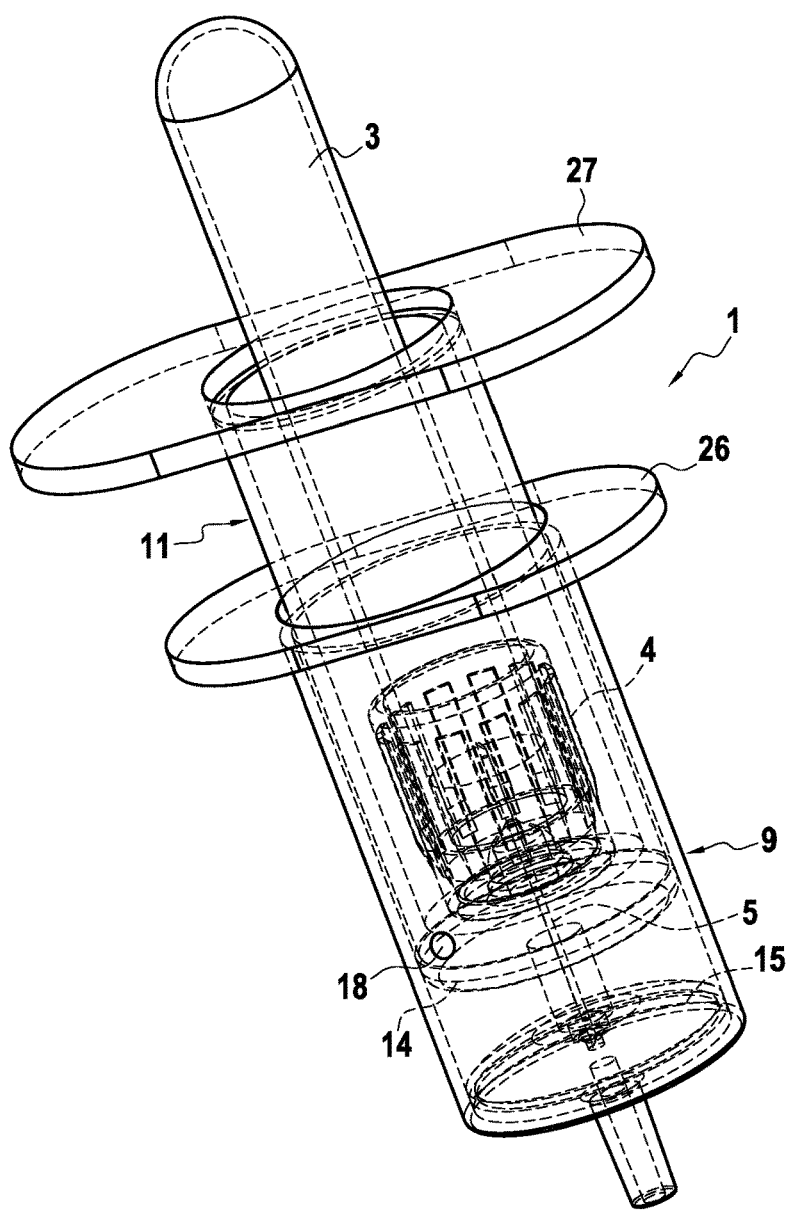
FIG. 2 is a perspective view showing an embodiment of the device in accordance with the invention for extracting a sample of blood contained in a container.
Figure 3:
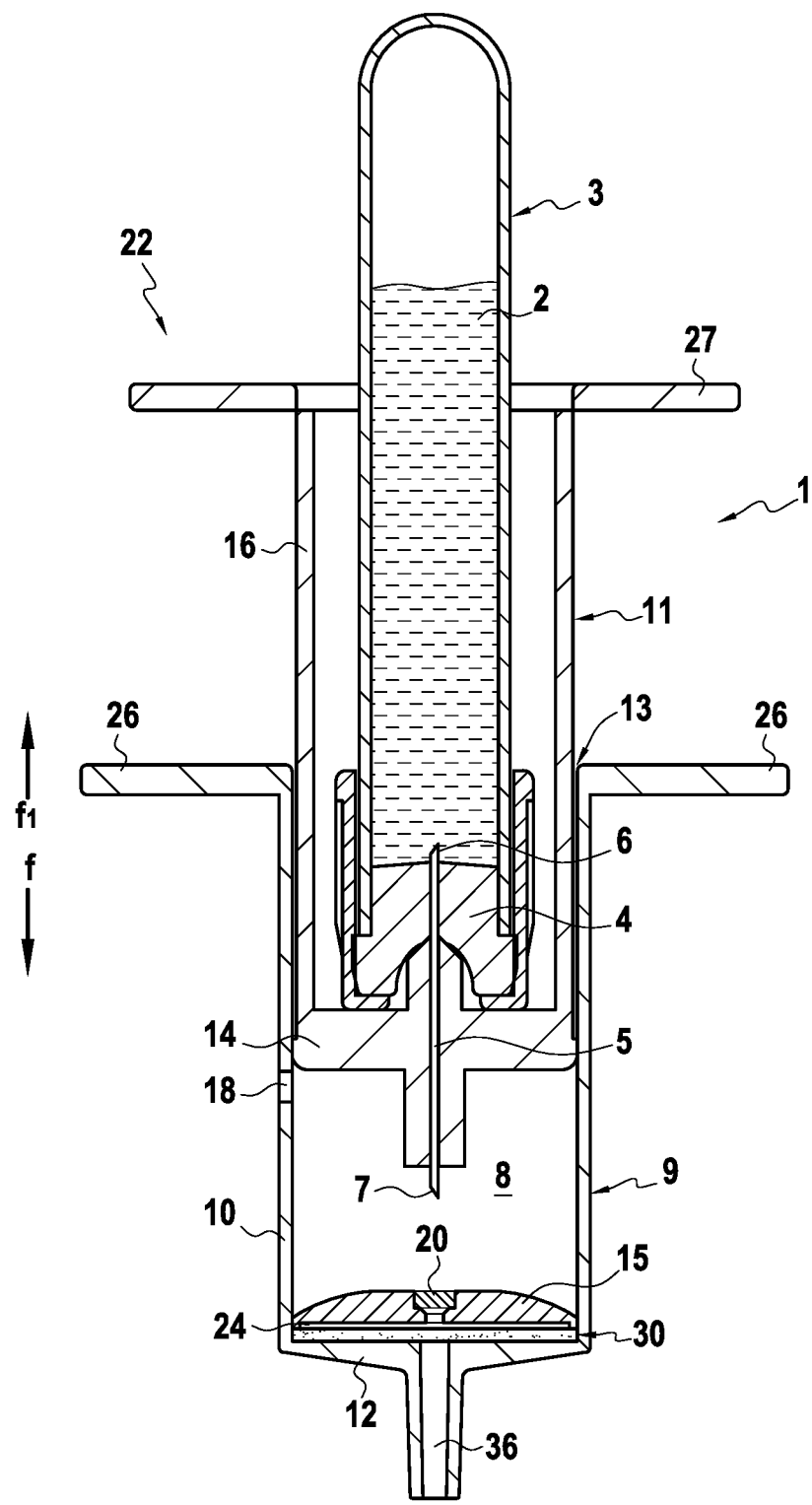
FIG. 3 is an elevation view in section showing the device in accordance with the invention in an initial extraction position.

In accordance with the invention, the device 1 includes a pressure chamber 8 for pressurizing a fluid contained in such a chamber. This pressure chamber 8 is defined between a cylinder 9 and a piston 11 that co-operates in leaktight manner with the cylinder 9. As can be seen in FIGS. 2 and 3, the cylinder 9 is in the form of a tube 10 of circular right cross-section that is provided with an end wall 12 at one end and with an opening 13 at its opposite end for passing the piston 11. The piston 11 has a rigid partition 14 optionally provided with a gasket and presenting a shape that is complementary to the tube 10 of the cylinder so that they co-operate together in leaktight manner. The tube 10 is provided at its end wall 12 with a closure partition 15 serving to co-operate with the rigid partition 14 of the piston and with the wall of the tube 10 situated between these partitions so as to define the pressure chamber 8 of variable volume.

According to a preferred embodiment characteristic, the piston 11 is provided with the hollow needle 5 having its distal end 6 facing away from the pressure chamber 8 and projecting from one side of the rigid partition 14. According to an advantageous embodiment characteristic, the length of the distal end 6 of the hollow needle 5 that projects from the rigid partition 14 is sufficient to pass through the plug 4 and penetrate into the inside of the container 3. The proximal end 7 of the hollow needle 5 extends towards the pressure chamber 8 and projects from the other side of the rigid partition 14. The hollow needle 5 is thus fastened in leaktight manner by any appropriate means to the rigid partition 14 and it passes right through it, projecting from the partition on both sides thereof.

According to another preferred embodiment characteristic, the piston 11 has a protective sleeve 16 surrounding the distal end 6 of the hollow needle 5 at a distance so as to define internally a reception volume for at least a portion of the container 3. Advantageously, the protective sleeve 16 extends from the rigid partition 14 over a height that is greater than the length of the distal end 6 of the hollow needle 5 so as to avoid any injury by this portion of the hollow needle.

From the above description, it can be seen that the piston 11 and the cylinder 9 are mounted to move relative to each other in translation in an approach direction represented by arrow f and in an opposite, separation direction represented by arrow f1. Thus, moving the piston 11 in the approach direction leads to a reduction in the volume of the chamber 8 and consequently to an increase in the pressure of the fluid inside the chamber 8.

It should be observed that while the device 1 is in use with the plug 4 of the container 3 having the distal end 6 of the hollow needle 5 passing therethrough, this pressure chamber 8 communicates via the hollow needle 5 with the inside of the container 3 so that its pressure has a value that is identical to the pressure in the chamber 8. Thus, an increase in the pressure of the fluid inside the chamber 8 leads to a corresponding increase of the pressure of the fluid inside the container 3.

According to an advantageous embodiment characteristic, the device 1 of the invention includes a system 18 for adjusting the pressure in the pressure chamber 8 and consequently in the container 3. In the example shown, the system 18 for adjusting the pressure in the pressure chamber 8 is provided by means of a through hole formed in the tube 10 to put the chamber 8 to atmospheric pressure so long as the piston 11 occupies a position set back from the hole 18. Thus, as soon as the position of the piston 11 is such that the chamber no longer communicates with the hole 18, the fluid can be compressed. This system 18 serves to adjust the pressure in the pressure chamber 8 by ensuring that it is set to atmospheric pressure so long as the spacing between the hollow needle 5 and a septum 20 does not reach a value as determined by the position of the hole 18.

Advantageously, the system 18 enables the value of the pressure in the pressure chamber 8 to be adjusted to a value that is variable. In an embodiment, the system includes a slide mounted to move in the travel direction of the piston and provided with a hole that is adapted to communicate with a slot formed in the tube 10 and that is closed by the slide with the exception of the hole. Moving the slide in translation adjusts the position of the hole for communicating with atmospheric pressure and consequently adjusts the volume of the chamber 8. In another embodiment, the closure partition 15 of the cylinder 9 is mounted to be movable relative to the tube 10 (e.g. by screw fastening) so as to enable the volume of the chamber 8 to be varied.

According to a characteristic of the invention, the pressure chamber 8 is provided with a septum 20 that is positioned so as to be penetrable by the proximal end 7 of the hollow needle 5 after it has been moved in the approach direction. For this purpose, the closure partition 15 of the cylinder 9 is provided with a septum 20 that is thus positioned facing the proximal end 7 of the hollow needle 5. For example, the septum 20 may be made in various ways, including by bi-injection, by overmolding, or by being inserted mechanically after molding.

Advantageously, the device 1 of the invention includes a system for guiding movement in translation of the proximal end 7 of the hollow needle 5 upstream from the septum 20. This guide system, which is not shown, is adapted to position the hollow needle so that the proximal end 7 passes correctly through the septum 20.

The device 1 of the invention includes a system 22 for causing the hollow needle 5 and the septum 20 to approach each other in such a manner that over a first stroke the pressure of the fluid inside the chamber 8 is increased up to a transfer pressure, and then over a subsequent stroke following the first, the hollow needle 5 passes through the septum 20 so that the hollow needle 5 leads into a blood distribution chamber 24 that is at a pressure that is lower than the transfer pressure. The distribution chamber 24 is thus separated from the pressure chamber 8, in particular by means of the septum 20, which is in contact on one side with the distribution chamber 24 and on its opposite side with the pressure chamber 8.

The system 22 for causing the hollow needle 5 and the septum 20 to approach each other exerts a mechanical thrust force on the hollow needle in the direction f and/or on the septum 20 in the direction f1. In the variant embodiment that is shown in the drawings, the approach system 22 is of manual type, however it is clear that the movement between the hollow needle 5 and the septum 20 could be motor-driven.

In order to facilitate manual application of a thrust force, the tube 10 of the cylinder 9 includes two external grip lugs 26 level with its opening 13, while the protective endpiece 16 is provided remote from the rigid partition 14 with a thrust collar 27. Conventionally, a thrust force is exerted on the collar 27 of the sleeve of the piston 11, while the cylinder 9 is held in position by the lugs 26. In this embodiment, a system is provided for viewing the penetration of the piston 11 into the cylinder 9 in order to control the amount of manual pressure that is applied. For example, graduations are marked on the piston 11 in order to visualize the penetration of the piston 11.

Figure 4:
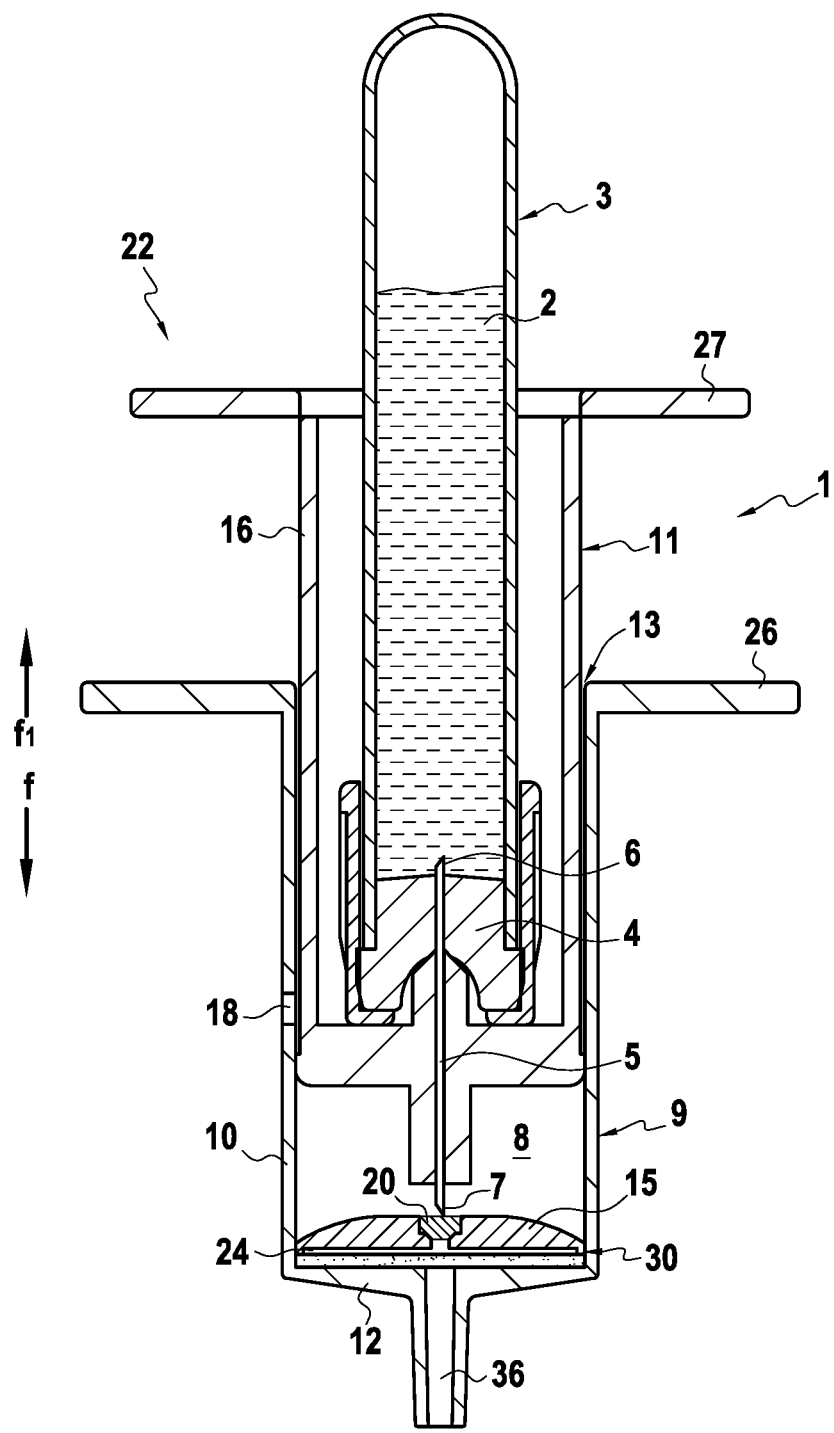
FIG. 4 is an elevation view in section showing the device in accordance with the invention in an intermediate extraction position.
Figure 5:
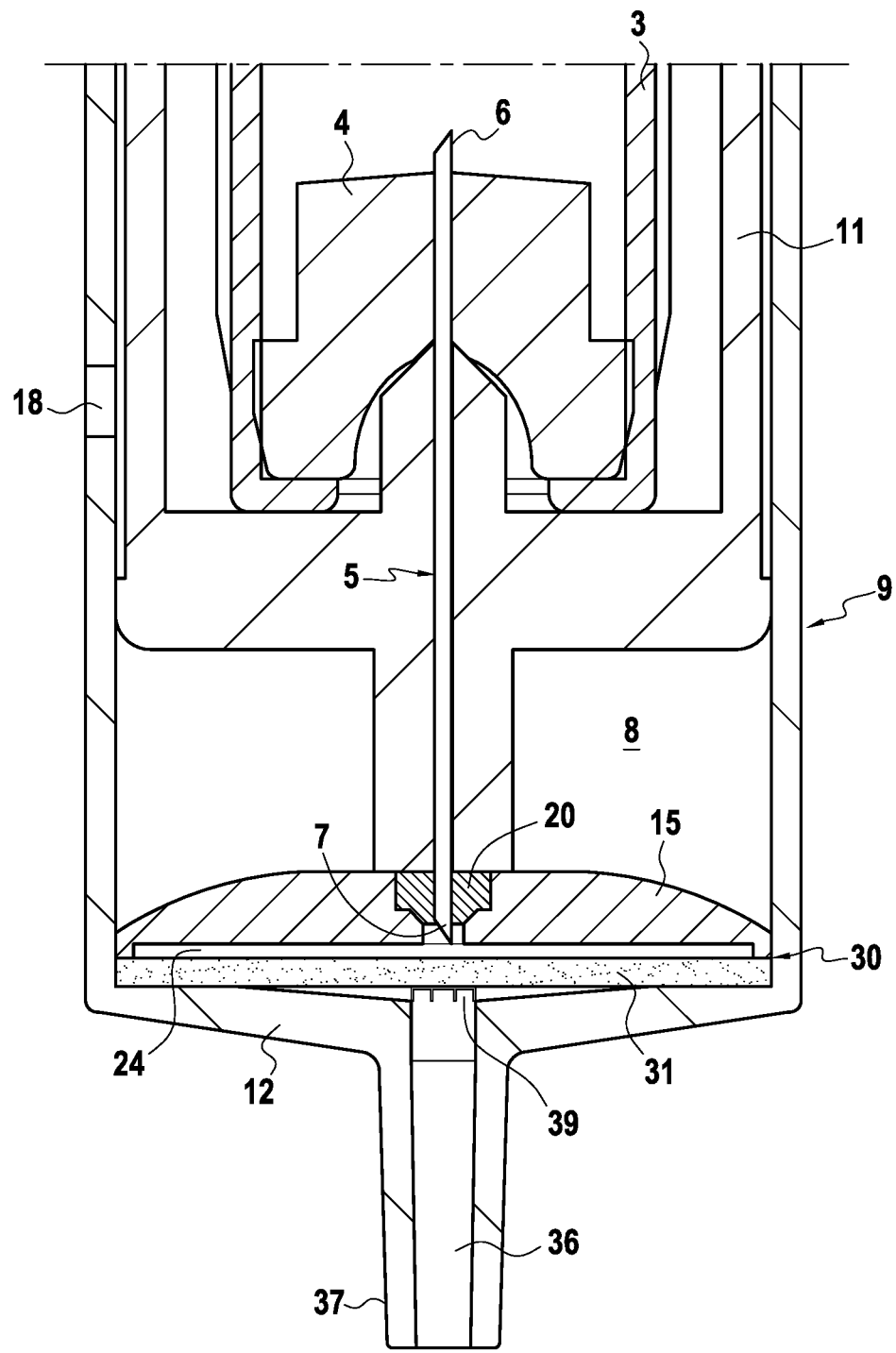
FIG. 5 is an elevation view on a larger scale in section showing the device in accordance with the invention in a position for extracting a portion of the blood sample contained in a container.

From the above description, it can be seen that the piston 11 is suitable for occupying:
- a first position as shown in FIG. 3 in which the chamber 8, and consequently the container 3, are set to atmospheric pressure via the hole 18;
- a second position, as shown in FIG. 2, enabling the pressure inside the chamber 8, and consequently inside the container 3, to be increased as the partitions 14 and 15 approach each other;
- a third position as shown in FIG. 4, in which the hollow needle 5 is positioned immediately prior to passing through the septum 20; and
- a fourth position as shown in FIG. 5 in which the hollow needle 5 passes through the septum 20 and communicates with the distribution chamber 24, which is advantageously at atmospheric pressure.

According to an advantageous embodiment characteristic, the device 1 of the invention includes a stop for limiting the approach movement of the partitions and 15 in a predetermined position in which the proximal end 7 of the hollow needle 5 passes through the septum 20 so as to open out into the distribution chamber 24 (FIG. 5). In the example shown in FIG. 4, the bottom end of the partition 14 comes directly into abutment against the partition 15. Another abutment system (not shown) could be made in any other suitable manner, e.g. by an arrangement on the sleeve 16 for coming to bear against the lugs of the cylinder 10.

According to an advantageous embodiment characteristic that can be better understood from the description below, the approach system 22 also serves to separate the hollow needle 5 relative to the septum 20 that can be penetrated by the needle. This system 22, which is adapted to separate the hollow needle 5 from the septum 20, exerts a mechanical thrust force on the hollow needle 5 in the direction f1 and/or on the septum 20 in the direction f. In the embodiment variant shown in the drawings, the separation system 22 is of the manual type, but it is clear that the movement between the hollow needle 5 and the septum 20 could be motor-driven.

The distribution chamber 24 is provided with the filter system 30 that serves to extract plasma from the blood transferred into the chamber.

As can be seen more clearly in FIG. 5, the filter system 30 comprises the filter medium 31 in accordance with the invention held in position by a support structure such as the end wall 12 of the cylinder 9. Advantageously, the filter medium 31 is mounted inside the distribution chamber 24 so as to extend at a distance from the septum, and in particular from the closure partition 15. Thus, the distribution chamber 24 presents a volume between the closure partition 15 and the top surface of the filter medium 31 for recovering the blood leaving the proximal end 7 of the hollow needle 5. This distribution chamber 24 serves to distribute the blood over the entire surface of the filter medium 31.

Figure 7:
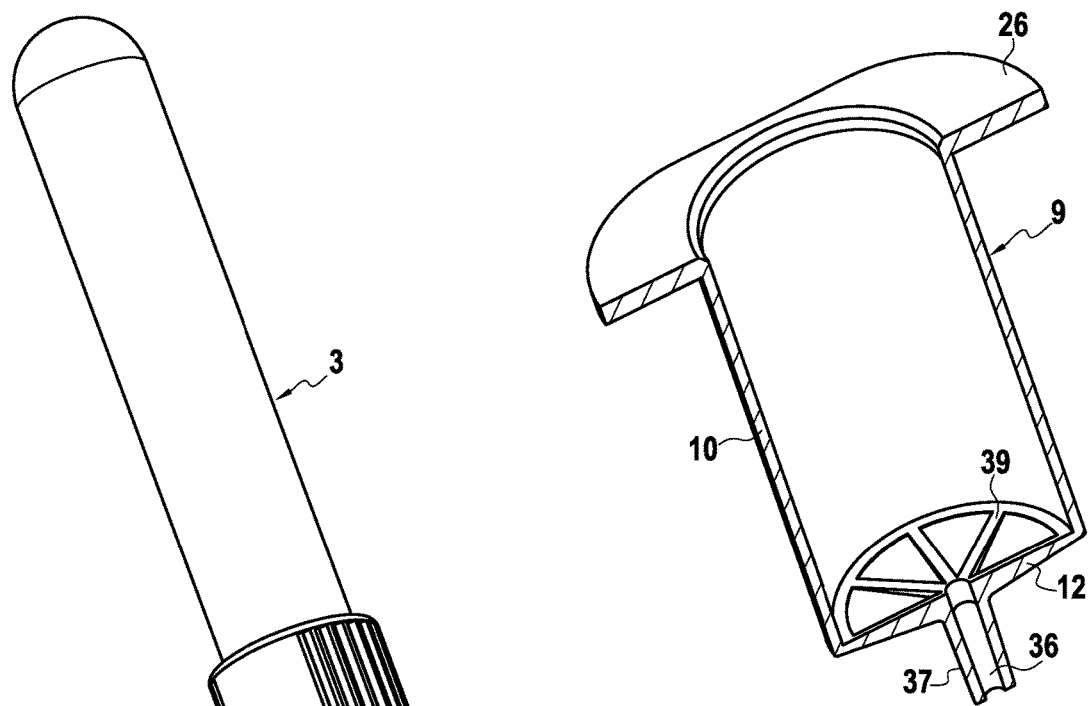
FIG. 7 is a section view of the cylinder for receiving the piston of the extraction device in accordance with the invention.
Figure 6:
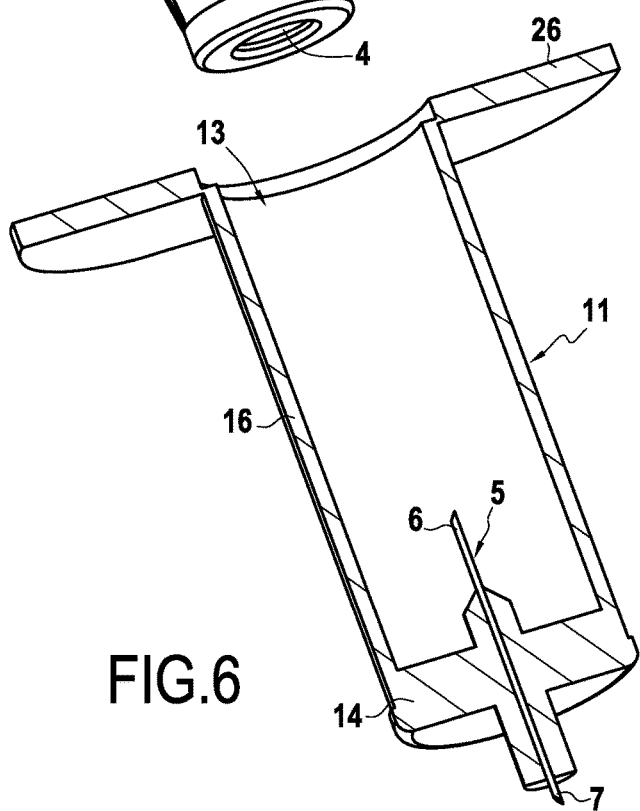
FIG. 6 is a perspective view showing how a container is mounted on the piston of the extraction device in accordance with the invention.

Advantageously, the end wall 12 of the cylinder 9 on which the filter medium 31 rests is curved towards an outlet orifice 36 for the filtered plasma, which orifice is formed in a tip 37 projecting from the end wall 12. The end wall 12 on which the filter medium 31 rests is preferably provided with ribs or spokes 39 on the end wall 12 so as to avoid the filter medium 31 clogging and so as to limit head loss (FIG. 7).

In the example shown in the drawings, the distribution chamber 24 is defined by a portion of the piston-receiving cylinder 9. It should be observed that it is possible to envisage making the chamber 24 as a separate unit that constitutes the filter system and that is fitted on the cylinder 9. A releasable connection for the distribution chamber 24 may be provided, in particular in order to make it easy to recover the filter medium, should it need to be subjected to subsequent analyses. Usually, the complete device is in the form of a disposable consumable, without there being any manipulation of the filter medium 31, such that such a releasable connection need not be provided.

The way in which the device 1 in accordance with the invention is used for transferring a portion of a sample of blood contained in the container 3 stems directly from the above description.

The transfer method consists in using the hollow needle 5 to put the inside of the container 3 into communication with the pressure chamber 8. For this purpose, the container 3 is inserted into the sleeve 16 until the distal end 6 of the hollow needle 5 passes through the plug 4. If the pressure chamber 8 is at atmospheric pressure because of the hole 18, then the container 3 is also placed at atmospheric pressure (FIG. 3).

Thereafter, the method consists in causing the hollow needle 5 to approach the septum 20 in order to increase the pressure inside the chamber 8, and consequently inside the container 3. Applying a thrust force to the piston 11 leads to it moving in the direction f, to a position beyond the hole 18, in which position the chamber 8 and the container 3 together form a hermetically sealed enclosure. Continued movement of the piston 11 in the direction f enables the pressure of the fluid to be increased with some of the fluid being transferred into the container 3 via the hollow needle 5. The piston 11 is moved along a stroke that is determined in such a manner that the piston 11 becomes located immediately in front of the passage for the hollow needle 5 through the septum 20. In this position, as shown in FIG. 4, the pressure inside the chamber 8 and the container 3 reaches a desired pressure value referred to as the "transfer" pressure. Typically, the transfer pressure lies in the range atmospheric pressure (in particular standard atmospheric pressure at sea level, namely $1.013 \times 10^5$ pascals (Pa)) to atmospheric pressure plus 3 bars.

The method then consists in continuing to cause the hollow needle 5 to approach the septum 20 so that the proximal end 7 of the hollow needle 5 passes through the septum 20 and opens out into the distribution chamber 24 (FIG. 5). Insofar as the pressure in this distribution chamber 24 presents a pressure (typically atmospheric pressure) that is lower than the transfer pressure in the chamber 8 and the container 3, a portion of the blood is transferred under the effect of this pressure difference from the container 3 into the distribution chamber 24. The blood coming from the container 3 thus passes through the hollow needle 5 and flows from the proximal end 7 into the distribution chamber 24 until pressures are balanced between the container 3 and the distribution chamber 24.

Since the distribution chamber 24 is provided with the filter system for extracting plasma from the blood recovered in the chamber 24, the blood passes through the filter medium 31, beginning by passing through the prefiltration zone 100 and then passing through the asymmetric zone 200, after which the plasma flows out from the outlet orifice 36.

In an advantageous variant of this extraction method, the method consists, at the end of the fluid flowing into the distribution chamber 24, in moving the hollow needle 5 away from the septum 20 so as to extract the hollow needle 5 from the septum 20 and cause it to communicate via its proximal end 7 with the inside of the pressure chamber 8. Insofar as the fluid inside the chamber 8 presents a pressure that is higher than the pressure in the container 3, some of this fluid passes through the hollow needle 5, thereby causing the blood contained in the needle 5 to return into the container 3. As a result, any liquid that might remain inside the needle is prevented from flowing out from the needle.

It should be observed that by means of the system 22 the device 1 of the invention provides the advantage of being able to adapt the pressure in the pressure chamber 8 as a function of the volume of fluid contained inside the container 3, which volume of fluid may vary as a result of successive extractions or as a function of the levels to which containers 3 are filled. This regulation can be performed visually or in automatic manner.

In a particular embodiment, the fluid in the pressure chamber 8 is air. Naturally, the fluid in the chamber 8 could be of a different kind, such as a blood that is not miscible with the liquid contained in the container 3. On the same lines, the fluid in the pressure chamber 8 may comprise a medium for processing the blood contained in the container 3, while still containing a quantity of gas that is sufficient to enable compression/pressurization.

In a variant implementation of the device 1, a calibration stage may be performed in order to control the initial pressure in the pressure chamber 8. Prior to putting the container 3 into communication with the pressure chamber 8, this stage seeks to place the septum 20 and the hollow needle 5 in a position of proximity, i.e. the hollow needle is placed just before passing through the septum 20. A pressurizing fluid is injected into the chamber 8 through the hollow needle 5 and from its distal end 6, causing the movable piston 11 to be positioned at a determined distance from the closure partition 15 in order to define a chamber with a desired volume of fluid.

From the above description, it can be seen that the device 1 of the invention makes it possible in complete safety to extract a portion of a sample of blood contained in a container 3. This extraction is performed in a manner that is simple and inexpensive since it merely involves mechanical thrust. The device 1 is preferably for single use with each container.

Advantageously, the device enables plasma to be extracted directly from a sample tube containing whole blood.

Tests have been performed with a filter medium of circular section and a diameter of 20 mm, the medium being made up of the following stack:

a prefiltration zone: three filters of glass microfibers sold by the supplier Ahlström under the reference 8964. Each of these filters had a density of 75 g·m$^{-2}$, and a thickness of 0.43 mm. They were subjected to prior treatment for fixing anti-red blood cell antibodies by immersing the filter in a solution containing said antibodies at 0.5 mg/mL in the presence of casein, followed by drying; and a zone of asymmetric pore size with greater pore size in contact with the above filter of glass microfibers: an asymmetric filter made of polysulfone sold by the supplier Pall forming part of the Vivid® range and of grade GX. The thickness of the filter was 330 μm±20 μm.

Tests with the filter medium using a device of the invention have shown that the device 1 of the invention makes it possible to extract at least 200 microliters (μL) of plasma in less than 3 minutes from a sample tube having a septum and containing a sample of whole blood. Furthermore, it has been possible to extract 200 μL of plasma four times in succession from a single 4 mL blood sample tube, using four successive filter devices 1. Use of the device 1 makes it possible in particular to increase the volume that is processed in given time.

Experiments performed with an incomplete filter medium (prefiltration zone not pretreated with reagents specific to red blood cells, no prefiltration zone, ...) have shown that the plasma is degraded in terms of quantity (small volume) and quality (a large amount of hemolysis or the presence of formed elements of blood, including red blood cells).

In particular, by way of comparison, tests performed without prior treatment of glass microfiber filters have shown that clogging occurs quickly in the Vivid® filter with only a small quantity of very hemolyzed plasma being recovered. Furthermore, tests performed without a Vivid® filter have shown that formed elements of blood pass through, including red blood cells.

The invention claimed is:

1. A filter medium comprising:
   two porous zones arranged in the form of a stack;
   a first porous zone, called "prefiltration", treated with at least one reagent presenting affinity for red blood cells and leading to red blood cells being captured or agglutinated on the prefiltration zone; and
   a second porous zone, called "asymmetric", presenting pore size that decreases transversely to its thickness, the portion of a higher pore size being positioned towards the prefiltration zone;
   wherein the minimum size of the pores in the prefiltration zone is greater than the maximum size of the pores in the asymmetric zone.

2. The filter medium according to claim 1, wherein the prefiltration zone presents a pore size greater than the size of red blood cells.

3. The filter medium according to claim 1, wherein the asymmetric zone presents a pore size in a portion of the asymmetric zone of maximum pore size that allows red blood cells to pass, and presents a pore size in a portion of the asymmetric zone of minimum pore size that is less than the size of blood cells.

4. The filter medium according to claim 1, wherein the reagents presenting affinity for red blood cells are binding partners specific to red blood cells.

5. The filter medium according to claim 1, wherein the prefiltration zone presents a thickness of from 0.3 mm to 5 mm.

6. The filter medium according to claim 1, wherein the asymmetric zone presents a thickness of from 0.1 mm to 5 mm.

7. The filter medium according to claim 1, wherein the prefiltration zone has a critical wetting surface tension between $50 \times 10^{-3}$ N·m$^{-1}$ and $100 \times 10^{-3}$ N·m$^{-1}$.

8. The filter medium according to claim 1, wherein the asymmetric zone has a critical wetting surface tension between $50 \times 10^{-3}$ N·m$^{-1}$ and $100 \times 10^{-3}$ N·m$^{-1}$.

9. The filter medium according to claim 1, wherein the prefiltration zone is constituted by a fiber material.

10. The filter medium according to claim 1, wherein the asymmetric zone comprises a porous material selected from synthetic polymers and from inorganic materials.

11. A filter system for filtering blood, enabling plasma to be recovered, comprising a chamber containing a filter medium according to any preceding claim and provided with an inlet for the blood to be filtered that is positioned towards the prefiltration zone, and with an outlet for plasma that is situated towards the asymmetric zone, the filter medium being positioned in the chamber in such a manner that the blood flows from the inlet to cross through both zones of the filter medium, with plasma being recovered at the outlet.

12. The filter system according to claim 11, wherein the blood is whole blood.

13. A method of obtaining plasma from a blood sample, the method implementing the system according to claim 11 in which the sample of blood is introduced into the filter system via the inlet, and plasma is recovered from the outlet.

14. The method according to claim 13, wherein the blood sample is a whole blood sample.

15. The filter medium according to claim 2, wherein the pore size is in a range of from 10 µm to 1 mm.

16. The filter medium according to claim 3, wherein the asymmetric zone presents a pore size, in the portion of the asymmetric zone of maximum pore size, that is in a range of from 10 µm to 100 µm.

17. The filter medium according to claim 3, wherein the asymmetric zone presents a pore size, in a portion of the asymmetric zone of minimum pore size, that is in a range of from 0.1 µm to 10 µm.

18. The filter medium according to claim 3, wherein the asymmetric zone presents a pore size, in a portion of the asymmetric zone of minimum pore size, that is less than the size of red blood cells.

19. The filter medium according to claim 4, wherein the reagents presenting affinity for red blood cells comprise a lectin.

20. The filter medium according to claim 19, wherein the lectin is hemagglutinin.

21. The filter medium according to claim 4, wherein the reagents presenting affinity for red blood cells comprise antibodies specific to antigens present on red blood cells.

22. The filter medium according to claim 5, wherein the prefiltration zone presents a thickness of from 1.2 mm to 3 mm.

23. The filter medium according to claim 6, wherein the asymmetric zone presents a thickness of from 0.2 mm to 3 mm.

24. The filter medium according to claim 7, wherein the prefiltration zone has a critical wetting surface tension of greater than $53 \times 10^{-3}$ N·m$^{-1}$.

25. The filter medium according to claim 8, wherein the asymmetric zone has a critical wetting surface tension of greater than $70 \times 10^{-3}$ N·m$^{-1}$.

26. The filter medium according to claim 9, wherein the fiber material is glass fiber material.

27. The filter medium according to claim 10, wherein the synthetic polymers are selected from the group consisting of polysulfones, polycarbonates, polyesters, polyolefins, polyamines, polyacrylics, and polyvinyls.

28. The filter medium according to claim 10, wherein the inorganic materials are selected from the group consisting of glasses, ceramics, and metals.

* * * * *